(12) United States Patent
Lee et al.

(10) Patent No.: US 9,945,656 B2
(45) Date of Patent: Apr. 17, 2018

(54) MULTI-FUNCTION SPECTROSCOPIC DEVICE

(71) Applicant: KOREA INSTITUTE OF INDUSTRIAL TECHNOLOGY, Cheonan-si (KR)

(72) Inventors: Ho Jae Lee, Cheonan-si (KR); Sang Seon Lee, Mokpo-si (KR)

(73) Assignee: KOREA INSTITUTE OF INDUSTRIAL TECHNOLOGY, Cheonan-si (KR)

( * ) Notice: Subject to any disclaimer, the term of this patent is extended or adjusted under 35 U.S.C. 154(b) by 0 days.

(21) Appl. No.: 15/518,875

(22) PCT Filed: Oct. 5, 2015

(86) PCT No.: PCT/KR2015/010497
§ 371 (c)(1),
(2) Date: Apr. 13, 2017

(87) PCT Pub. No.: WO2016/068504
PCT Pub. Date: May 6, 2016

(65) Prior Publication Data
US 2017/0234674 A1 Aug. 17, 2017

(30) Foreign Application Priority Data
Oct. 30, 2014 (KR) .................. 10-2014-0148936

(51) Int. Cl.
*G01B 9/02* (2006.01)
*G01N 21/45* (2006.01)
(Continued)

(52) U.S. Cl.
CPC .......... *G01B 9/02044* (2013.01); *G01B 11/06* (2013.01); *G01B 11/2441* (2013.01); *G01N 21/45* (2013.01); *G01N 2201/068* (2013.01)

(58) Field of Classification Search
CPC .............. G01B 9/02044; G01B 11/2441; G01B 11/06; G01N 21/45; G01N 2201/068
See application file for complete search history.

(56) References Cited

U.S. PATENT DOCUMENTS

2003/0053053 A1* 3/2003 Opsal .................. G01N 21/211
356/369
2004/0150820 A1* 8/2004 Nikoonahad ...... G01N 21/8806
356/364
(Continued)

FOREIGN PATENT DOCUMENTS

JP 11-230829 8/1999
JP 2002-286408 10/2002
(Continued)

*Primary Examiner* — Kara E Geisel
*Assistant Examiner* — Dominic J Bologna
(74) *Attorney, Agent, or Firm* — Lex IP Meister, PLLC

(57) ABSTRACT

A multi-function spectroscopic device includes a first lens installed in an emission direction of parallel light and focusing the light in a center portion thereof, a second lens disposed to face the first lens and, a reference mirror installed to face the second lens, a beam splitter installed between the first lens and the second lens, a third lens focusing light which moves through the beam splitter onto a measurement object, a fourth lens focusing light which is reflected by the measurement object and reversely moves through the third lens and the beam splitter, a fifth lens converting light which is diffused through a second focus of the fourth lens into parallel light, and a diffraction grating obliquely disposed with respect to a light axis of the fifth lens and diffracting parallel light which moves through the fifth lens and split the parallel light.

8 Claims, 2 Drawing Sheets

(51) Int. Cl.
*G01B 11/24* (2006.01)
*G01B 11/06* (2006.01)

(56) References Cited

U.S. PATENT DOCUMENTS

| | | | | |
|---|---|---|---|---|
| 2005/0254049 | A1* | 11/2005 | Zhao | G01N 21/211 |
| | | | | 356/369 |
| 2005/0254050 | A1* | 11/2005 | Fielden | G01J 3/10 |
| | | | | 356/369 |
| 2005/0254065 | A1* | 11/2005 | Stokowski | G01N 21/95684 |
| | | | | 356/601 |
| 2011/0001988 | A1* | 1/2011 | Pahk | G01B 11/0625 |
| | | | | 356/630 |
| 2013/0021602 | A1* | 1/2013 | Dribinski | G02F 1/37 |
| | | | | 356/237.3 |

FOREIGN PATENT DOCUMENTS

| | | |
|---|---|---|
| KR | 10-1998-0010357 | 4/1998 |
| KR | 10-2009-0087664 | 8/2009 |
| KR | 10-0916618 | 9/2009 |
| KR | 10-2013-0039005 | 4/2013 |

\* cited by examiner

MULTI-FUNCTION SPECTROSCOPIC DEVICE

TECHNICAL FIELD

The present invention relates to a multi-function spectroscopic device, and more particularly, to a multi-function spectroscopic device configured to support measurement of a film thickness, a refractive index, and a surface shape.

BACKGROUND ART

Generally, in the case of a multilayer structure including a multilayer thin film such as a semiconductor, various measurement methods are used for inspecting a performance factors such as a film thickness, a surface shape, and a refractive index of a film.

A method of measuring a thickness and a shape using an interferometer is disclosed in Korean Patent No. 10-0916618.

Meanwhile, there are a method of analyzing a thickness and a refractive index by light being made perpendicularly incident on a measurement object and detecting an intensity of light reflected from the measurement object, and a method of measuring a thickness and a refractive index by light being made obliquely incident on a measurement object and analyzing polarization and intensity of light reflected from the measurement object, instead of a method using the interferometer.

However, since conventional devices for measuring a film thickness, a refractive index, and a surface shape are independently formed according to the above-described application manner, there is a disadvantage in that an integrated structure, which can be selectively used according to a required specification such as a level of accuracy required for a measurement object, cannot be provided.

DISCLOSURE

Technical Problem

The present invention is directed to providing a multi-function spectroscopic device capable of supporting various measurement methods while having a simple structure.

Technical Solution

The present invention provides a multi-function spectroscopic device including: a parallel light generation part configured to generate and emit parallel light; a first lens installed in an emission direction of the parallel light emitted by the parallel light generation part and configured to focus the light in a center portion thereof with respect to a light axis of the parallel light; a second lens disposed to face the first lens and configured to convert light which moves through a first focus of the first lens and is diffused into parallel light; a reference mirror installed to face the second lens to reflect light which moves through the second lens; a beam splitter installed between the first lens and the second lens and disposed to reflect some light which moves through the first lens in a direction intersecting a light axis of the first lens, and to transmit the remaining light toward the second lens; a third lens configured to focus light which moves through the beam splitter onto a measurement object; a fourth lens configured to focus light which is reflected by the measurement object and reversely moves through the third lens and the beam splitter; a first light path switch configured to switch a light path so that light which is generated by the parallel light generation part, moves toward a region other than the first lens, does not move through the first lens, and is reflected by the beam splitter to move is obliquely incident on a surface of the measurement object; and a second light path switch configured to switch a light path of light which moves from the first light path switch, moves through the measurement object, and obliquely moves with respect to a light axis of the third lens to move in a direction parallel to the light axis of the third lens.

The first light path switch may include a first inclined mirror disposed to reflect light which is reflected by the beam splitter and moves so that the light is obliquely incident on the surface of the measurement object, and the second light path switch may include a second inclined mirror obliquely disposed to reflect light which moves from the first inclined mirror, moves through the measurement object, and obliquely moves with respect to the light axis of the third lens to move in the direction parallel to the third light axis and move the beams toward the fourth lens.

One aspect of the present invention provides a multi-function spectroscopic device including: a fifth lens configured to convert light which is diffused through a second focus of the fourth lens into parallel light; and a diffraction grating obliquely disposed with respect to a light axis of the fifth lens and configured to diffract parallel light which moves through the fifth lens and split the parallel light. In addition, the multi-function spectroscopic device includes a slit in which a transmission hole configured to transmit light through the second focus as a center thereof is formed at a point of the second focus of the fourth lens.

The multi-function spectroscopic device may further include: a sixth lens configured to focus zeroth diffracted light which moves through the diffraction grating; and a seventh lens configured to focus first diffracted light which moves through the diffraction grating.

The multi-function spectroscopic device may further include: first and second light detectors configured to detect light respectively focused by the sixth lens and the seventh lens; a first shutter configured to move into and out of a region between the parallel light generation part and the first lens and to transmit or block light, which is generated by the parallel light generation part and moves toward a region other than the first lens; and a second shutter configured to move into and out of a region between the second lens and the reference mirror and to transmit light, which moves through the second lens, toward the reference mirror, or to absorb the light.

Another aspect of the present invention provides a multi-function spectroscopic device including: a light detector configured to detect light which moves through the fourth lens, wherein the parallel light generation part includes: a light source configured to change a wavelength of light and emit the light; and a light source driver configured to drive the light source so that the wavelength of the light emitted by the light source is changed according to a predetermined change condition and the light is emitted.

Advantageous Effects

A multi-function spectroscopic device according to the present invention provides an advantage in that a film thickness, a surface shape, and a refractive index can be measured by using a desired measurement method using an integrated optical system.

MODES OF THE INVENTION

Hereinafter, a multi-function spectroscopic device according to an exemplary embodiment of the present invention will be described in more detail with reference to the accompanying drawings.

Figure 1:
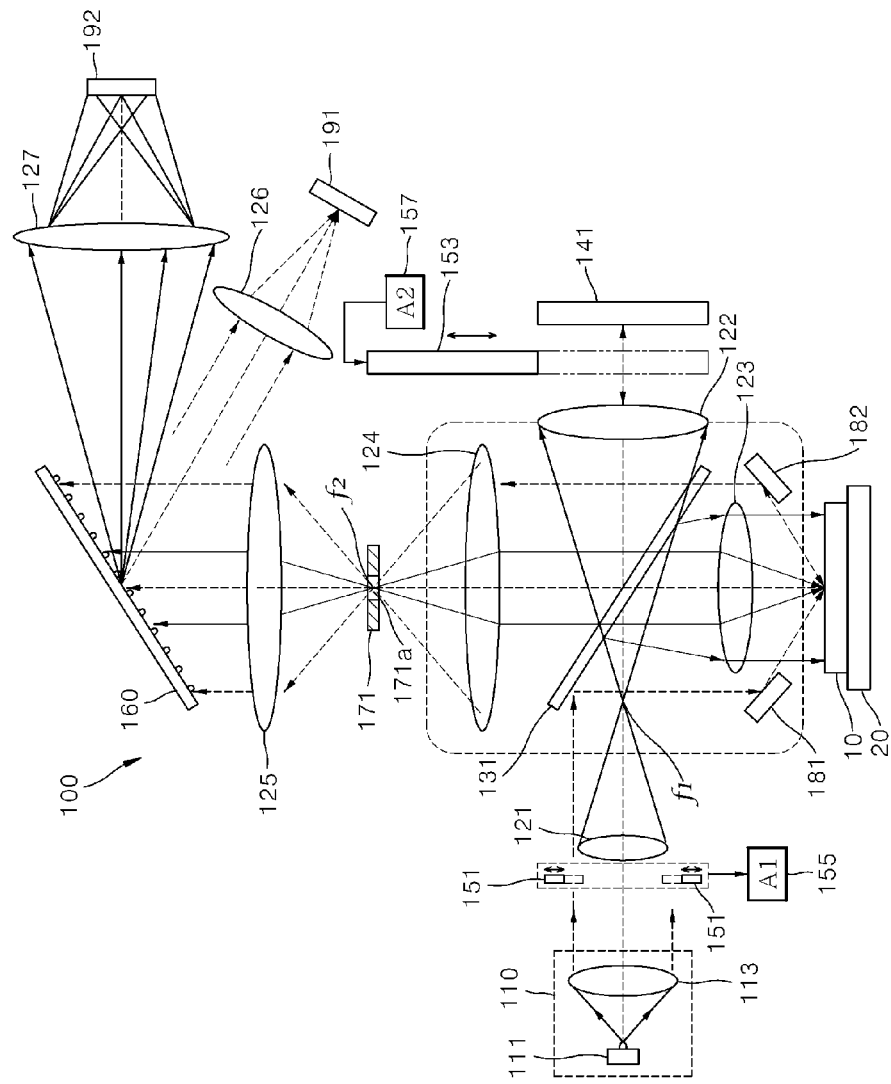
FIG. 1 is a view illustrating a multi-function spectroscopic device according to one embodiment of the present invention.

FIG. 1 is a view illustrating a multi-function spectroscopic device according to one embodiment of the present invention.

Referring to FIG. 1, a multi-function spectroscopic device 100 according to the present invention includes a parallel light generation part 110, first to seventh lenses 121 to 127, a beam splitter 131, a reference mirror 141, a diffraction grating 160, a slit 171, and first and second inclined mirrors 181 and 182.

The parallel light generation part 110 generates and emits parallel light.

The parallel light generation part 110 includes a light source 111 and a collimating lens 113 configured to convert light emitted by the light source 111 into parallel light.

The light source 111 employs a wide band light source configured to emit multi-wavelength light.

For example, the light source 111 may employ a wide band light source configured to emit light with a wide band wavelength of 400 to 800 nm.

The parallel light generation part 110 may also employ a laser device configured to emit parallel light beams unlike the illustrated example.

The first lens 121 is installed in a direction of a light axis of the parallel light emitted from the parallel light generation part 110, that is, a light axis of the first lens 121 is the same as that of the collimating lens 113, and thus light in a center portion thereof is focused onto a first focus f1 with respect to the light axis of the parallel light.

Here, an outer diameter of the first lens 121 is less than an area of a cross section of the parallel light generated by the parallel light generation part 110.

In this case, some of the parallel light generated by the parallel light generation part 110 moves through the first lens 121, and the remaining light which moves through a region extending from the first lens 121 moves without passing through the first lens 121.

The second lens 122 is disposed on the same line as the light axis of the first lens 121 to face the first lens 121, and is configured to convert light diffused through the first focus f1 of the first lens 121 into parallel light and emit the parallel light toward the reference mirror 141.

The reference mirror 141 is installed to face the second lens 122 so that parallel light incident thereon through the second lens 122 is reflected back toward the second lens 122.

The beam splitter 131 is installed between the first lens 121 and the second lens 122, and an extension direction of the beam splitter 131 is inclined with respect to the light axis of the first lens 121 for the beam splitter 131 to reflect some light which moves through the first lens 121 to move in a direction perpendicularly intersecting the light axis of the first lens 121, and to transmit some of the remaining light.

The beam splitter 131 is formed in a size suitable for reflecting even light which is emitted from parallel light generation part 110 and does not move through the first lens 121.

The third lens 123 is installed under the beam splitter 131 in a direction perpendicular to the light axis of the first lens 121 and is configured to focus light which moves through the beam splitter 131 onto a measurement object 10.

The fourth lens 124 is installed at a side opposite the third lens 123 with respect to the beam splitter 131 and is configured to focus light which is reflected by the measurement object 10 and moves through the third lens 123 and the beam splitter 131 onto a second focus f2.

Here, the second focus f2 is a focus of the fourth lens.

In addition, the fourth lens 124 has a size suitable for focusing even light which moves through the second inclined mirror 182.

The fifth lens 125 converts light diffused through the second focus f2 of the fourth lens 124 into parallel light and emits the parallel light toward the diffraction grating 160.

The diffraction grating 160 is disposed to be inclined, for example, by an inclination angle of 45° with respect to a light axis of the fifth lens 125 and is configured to split parallel light which moves through the fifth lens 125 by diffracting the parallel light.

The sixth lens 126 focuses zeroth diffracted light which moves through the diffraction grating 160.

The seventh lens 127 focuses first diffracted light which moves through the diffraction grating.

The first inclined mirror 181 is applied as a first light path switch and is disposed to reflect light which is generated by the parallel light generation part 110 to move without passing through the first lens 121 and to move by being reflected by the beam splitter 131 so that the light is obliquely incident on a surface of the measurement object 10.

It is preferable for the first inclined mirror 181 to be provided such that an angle between an extension line along a surface on which light is incident and a light axis of the third lens 123 ranges from 50° to 70°.

The second inclined mirror 182 is applied as a second light path switch and is obliquely disposed to reflect light which moves from the first inclined mirror 181, moves through the measurement object 10, to move in a direction parallel to the light axis of third lens 123 and move toward the fourth lens 124.

The slit 171, which is installed at a point of the second focus f2 of the fourth lens 124 and in which a transmission hole 171a which transmits light through the second focus f2 as a center thereof is formed.

It is preferable for the transmission hole 171a formed in the slit 171 to have a rectangular shape having a width of 5 to 10 μm and a length of 5 to 10 mm.

A first light detector 191 detects light focused by the sixth lens 126.

A second light detector 192 detects light focused by the seventh lens 127.

The first and second light detectors 191 and 192 may employ a charge coupled device (CCD) camera and the like capable of generating and outputting an electric signal corresponding to light incident thereon or an element capable of detecting an intensity of light or an intensity of light by wavelength.

A first shutter 151 is provided to transmit or block light, which is generated by the parallel light generation part 110 and moves toward a region other than the first lens 121, while moving into and out of a region between the parallel light generation part 110 and the first lens 121.

That is, the first shutter 151 is installed to allow or block light, which is generated by the parallel light generation part 110 and moves toward the region other than the first lens 121, to move toward the beam splitter 131.

Otherwise, the first shutter 151 may also be installed to transmit only light which moves toward the region other than the first lens 121 and to block light which moves toward the first lens 121 among the light which is generated by the parallel light generation part 110 while moving into and out of the region between the parallel light generation part 110 and the first lens 121.

The first shutter 151 is installed to allow light to move toward the first inclined mirror 181 or to be blocked while being moved forward or backward by a first actuator A1 155.

A second shutter 153 is installed to transmit light, which moves through the second lens 122, toward the reference mirror 141, or to absorb the light to be blocked while moving into and out of a region between the second lens 122 and the reference mirror 141.

The second shutter 153 is also installed to allow light to move toward the reference mirror 141 or to be blocked while being moved forward or backward by the second actuator A2 157.

Reference numeral 20 denotes a seating table configured to horizontally move the measurement object 10.

When the measurement object 10 is a thick film having a film thickness of 0.1 μm or more, and the film thickness or a refractive index of the measurement object 10 is measured using only light which moves through the third lens 123, the multi-function spectroscopic device 100 measures the film thickness or the refractive index by blocking light, which is moved toward the first inclined mirror 181 by the first shutter 151, and detecting light which moves through the diffraction grating 160.

In addition, when the measurement object 10 is a thin film having a film thickness less than 0.1 μm, the film thickness or the refractive index of the measurement object 10 is measured by light being made to be obliquely incident on the measurement object 10 through the first inclined mirror 181.

In addition, when an interferometer is applied, the second shutter 153 is disposed at a position other than a region toward which the second lens 122 emits light, and when the interferometer is not applied, the second shutter 153 is disposed at a position at which the region toward which the second lens 122 emits light is blocked.

Figure 2:
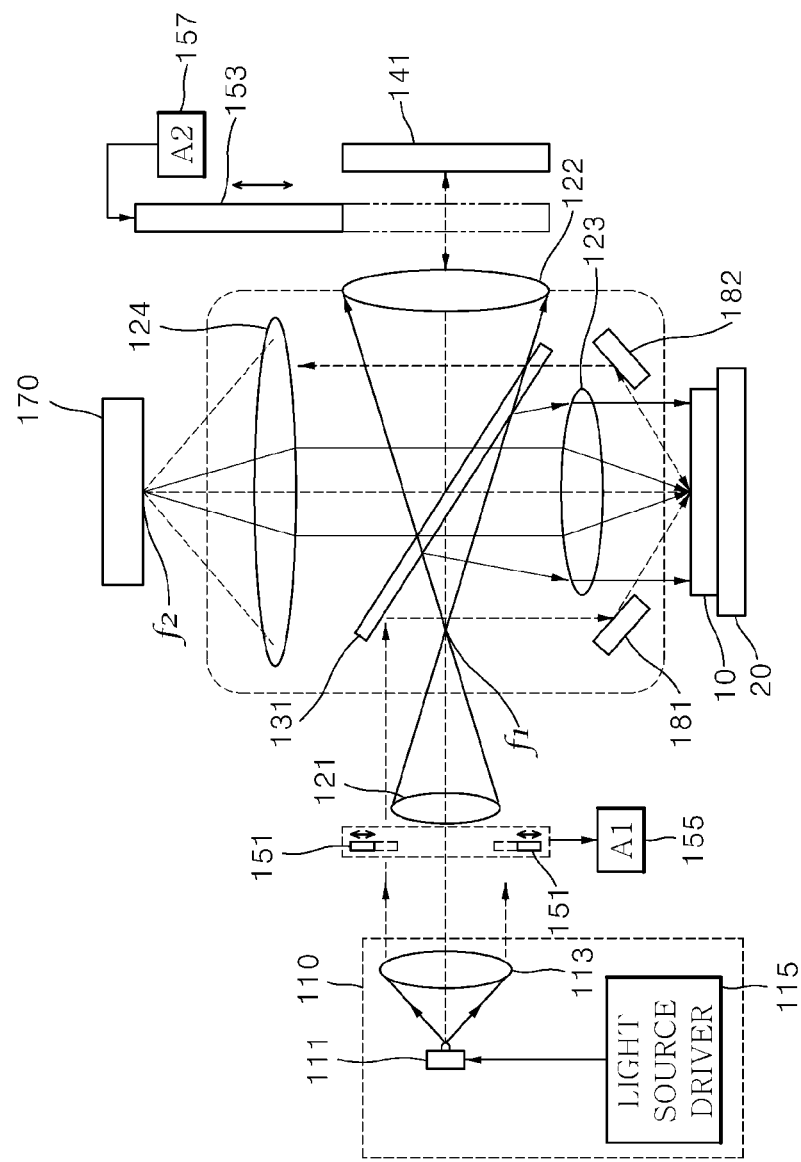
FIG. 2 is a view illustrating a multi-function spectroscopic device according to another embodiment of the present invention.

Meanwhile, another embodiment of the present invention is illustrated in FIG. 2. Components configured to perform the same functions as that in the previous drawing will be referred with the same reference numerals.

Referring to FIG. 2, a multi-function spectroscopic device includes a light detector 170 which detects light which moves through a fourth lens 124, and faces the fourth lens.

Here, the light detector 170 may employ a CCD camera.

In addition, a parallel light generation part 110 includes a light source 111 configured to change a wavelength of light and emit the light, and a light source driver 115 configured to drive the light source 111 so that the wavelength of the light emitted by the light source 111 is changed according to a predetermined change condition and the light are emitted.

In this case, since the parallel light generation part 110 emits light with a changed wavelength, the light detector 170 may detect light which is reflected by a measurement object 10 by corresponding to the changed wavelength, and thus, data of a spectroscopic effect corresponding to a diffraction grating can be obtained.

Since the multi-function spectroscopic device 100 supports various measurement methods, the multi-function spectroscopic device 100 provides an advantage in that a film thickness, a surface shape, and a refractive index can be measured by using a desired measurement method.

The invention claimed is:

1. A multi-function spectroscopic device comprising:
a parallel light generation part configured to generate and emit parallel light;
a first lens installed in an emission direction of the parallel light emitted by the parallel light generation part and configured to focus the light in a center portion thereof with respect to a light axis of the parallel light;
a second lens disposed to face the first lens and configured to convert light which moves through a first focus of the first lens and is diffused, into parallel light;
a reference mirror installed to face the second lens to reflect light which moves through the second lens;
a beam splitter installed between the first lens and the second lens and disposed to reflect some light which moves through the first lens in a direction intersecting a light axis of the first lens, and to transmit the remaining light toward the second lens;
a third lens configured to focus light which moves through the beam splitter onto a measurement object;
a fourth lens configured to focus light which is reflected by the measurement object and reversely moves through the third lens and the beam splitter;
a first light path switch configured to switch a light path so that light which is generated by the parallel light generation part, moves toward a region other than the first lens, does not move through the first lens, and is reflected by the beam splitter to move is obliquely incident on a surface of the measurement object; and
a second light path switch configured to switch a light path of light which moves from the first light path switch, moves through the measurement object, and obliquely moves with respect to a light axis of the third lens to move in a direction parallel to the light axis of the third lens.

2. The multi-function spectroscopic device of claim 1, wherein:
the first light path switch includes a first inclined mirror disposed to reflect light which is reflected by the beam splitter and moves so that the light is obliquely incident on the surface of the measurement object; and
the second light path switch includes a second inclined mirror obliquely disposed to reflect light which moves from the first inclined mirror, moves through the measurement object, and obliquely moves with respect to the light axis of the third lens to move in the direction parallel to the third light axis and move the beams toward the fourth lens.

3. The multi-function spectroscopic device of claim 2, further comprising:
a fifth lens configured to convert light which is diffused through a second focus of the fourth lens into parallel light; and
a diffraction grating obliquely disposed with respect to a light axis of the fifth lens and configured to diffract parallel light which moves through the fifth lens and split the parallel light.

4. The multi-function spectroscopic device of claim 3, further comprising a slit in which a transmission hole configured to transmit light through the second focus as a center thereof is formed at a point of the second focus of the fourth lens.

5. The multi-function spectroscopic device of claim 4, further comprising:
   a sixth lens configured to focus zeorth diffracted light which moves through the diffraction grating; and
   a seventh lens configured to focus first diffracted light which moves through the diffraction grating.

6. The multi-function spectroscopic device of claim 5, further comprising first and second light detectors configured to detect light respectively focused by the sixth lens and the seventh lens.

7. The multi-function spectroscopic device of claim 2, further comprising:
   a first shutter configured to move into and out of a region between the parallel light generation part and the first lens and to transmit or block light which is generated by the parallel light generation part and moves toward a region other than the first lens; and
   a second shutter configured to move into and out of a region between the second lens and the reference mirror and to transmit light, which moves through the second lens, toward the reference mirror, or to absorb the light.

8. The multi-function spectroscopic device of claim 2, further comprising a light detector configured to detect light which moves through the fourth lens,
   wherein the parallel light generation part includes:
   a light source configured to change a wavelength of light and emit the light; and
a light source driver configured to drive the light source so that the wavelength of the light emitted by the light source is changed according to a predetermined change condition and the light is emitted.

* * * * *